(12) United States Patent
Oyama

(10) Patent No.: US 12,178,406 B2
(45) Date of Patent: Dec. 31, 2024

(54) ENDOSCOPE BENDING PORTION AND ENDOSCOPE

(71) Applicant: OLYMPUS CORPORATION, Tokyo (JP)

(72) Inventor: Katsumi Oyama, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 905 days.

(21) Appl. No.: 17/220,422

(22) Filed: Apr. 1, 2021

(65) Prior Publication Data

US 2021/0219818 A1     Jul. 22, 2021

Related U.S. Application Data

(63) Continuation of application No. PCT/JP2018/037178, filed on Oct. 4, 2018.

(51) Int. Cl.
    *A61B 1/008*     (2006.01)
    *A61B 1/005*     (2006.01)

(52) U.S. Cl.
    CPC ............ *A61B 1/008* (2013.01); *A61B 1/0057* (2013.01)

(58) Field of Classification Search
    CPC ...... A61B 1/008; A61B 1/0055; A61B 1/0057
    See application file for complete search history.

(56) References Cited

U.S. PATENT DOCUMENTS

| | | | |
|---|---|---|---|
| 2005/0075538 A1* | 4/2005 | Banik | A61B 1/0052 600/152 |
| 2010/0056868 A1* | 3/2010 | Kitagawa | G02B 23/2407 600/141 |
| 2017/0095138 A1* | 4/2017 | Nakade | A61B 1/0052 |
| 2018/0042451 A1* | 2/2018 | Cuscuna | A61B 1/0011 |
| 2020/0046209 A1* | 2/2020 | Fancher | A61B 1/05 |

(Continued)

FOREIGN PATENT DOCUMENTS

| | | |
|---|---|---|
| JP | H06-319684 A | 11/1994 |
| JP | 2008-279055 A | 11/2008 |

(Continued)

OTHER PUBLICATIONS

International Search Report dated Dec. 11, 2018 issued in PCT/JP2018/037178.

*Primary Examiner* — John P Leubecker
(74) *Attorney, Agent, or Firm* — Scully, Scott, Murphy & Presser, P.C.

(57) ABSTRACT

A bending tube is constructed of a first bending piece including a first upper-side opening and a first lower-side opening formed on an outer surface in a longitudinal axis direction, and a first upper-side wire accommodating groove and a first lower-side wire accommodating groove continuous with a first upper-side opening and a first lower-side opening respectively and formed in a direction crossing two up and down bending directions at an angle of 90 degrees, and a second bending piece including a second upper-side opening and a second lower-side opening formed on an outer surface in the longitudinal axis direction, and a second upper-side wire accommodating groove and a second lower-side wire accommodating groove continuous with a second upper-side opening and a second lower-side opening respectively and formed in a direction crossing the two up and down bending directions at an angle of 270 degrees.

19 Claims, 17 Drawing Sheets

(56) References Cited

U.S. PATENT DOCUMENTS

2021/0219821 A1\* 7/2021 Appling ................ A61B 1/0056
2023/0284885 A1\* 9/2023 Huang ................. A61B 1/0057

FOREIGN PATENT DOCUMENTS

| | | |
|---|---|---|
| JP | 2009-160224 A | 7/2009 |
| JP | 2010-017401 A | 1/2010 |
| JP | 2010-220827 A | 10/2010 |
| JP | 2011-156269 A | 8/2011 |
| JP | 2011-200585 A | 10/2011 |
| JP | 2014-023919 A | 2/2014 |
| WO | 2008/139768 A1 | 11/2008 |
| WO | 2009/087880 A1 | 7/2009 |
| WO | 2012/056860 A1 | 5/2012 |

\* cited by examiner

ENDOSCOPE BENDING PORTION AND ENDOSCOPE

CROSS REFERENCE TO RELATED APPLICATION

This application is a continuation application of PCT/JP2018/037178 filed on Oct. 4, 2018, the entire contents of which are incorporated herein by this reference.

BACKGROUND OF THE INVENTION

1. Field of the Invention

The present invention relates to an endoscope bending portion, bending operation of which is performed by pulling or relaxing a pulling wire, and an endoscope.

2. Description of the Related Art

Conventionally, endoscopes have been used to observe a target region inside a subject by inserting an elongated insertion portion into the subject such as a body cavity or to perform various treatments using a treatment instrument inserted into a treatment instrument channel as needed.

As this kind of endoscope, a configuration in which a distal end portion, a bending portion and a flexible tube portion are disposed in order from a distal end side is widely adopted. When an insertion portion of such an endoscope is inserted into the subject, an operator grasps an operation portion by one hand, grasps the flexible tube portion by the other hand and pushes the insertion portion into the subject. In that case, the operator operates an operation lever or the like disposed at the operation portion by the hand grasping the operation portion, and can thereby cause the bending portion to bend in a desired direction.

As disclosed, for example, in Japanese Patent Application Laid-Open Publication No. 2011-156269, such bending operation of the bending portion is performed by pulling or relaxing a pulling wire inserted through the insertion portion in conjunction with an operation lever or the like. Thus, two or four wire guides protruding in an inner diameter direction are provided in each bending piece that constitutes the bending portion and two or four pulling wires are inserted through each wire guide. A proximal end side of each pulling wire is connected to the operation lever or the like and a distal end side of each pulling wire is fixed inside the distal end portion, and it is thereby possible to pull or relax each pulling wire in conjunction with the operation lever or the like and cause the bending portion to perform bending operation.

SUMMARY OF THE INVENTION

An endoscope bending portion according to an aspect of the present invention is an endoscope bending portion including a plurality of bending elements connected in a longitudinal axis direction, the endoscope bending portion being enabled to bend in two bending directions by pulling a wire. Each of the plurality of bending elements includes an opening formed on an outer surface in the longitudinal axis direction, a first bending element including a first wire accommodating groove continuous with the opening and formed at a first position crossing the bending direction at 45 degrees to 135 degrees, and a second bending element including a second wire accommodating groove continuous with the opening and formed at a second position crossing the bending direction at 225 degrees to 315 degrees. The first bending element and the second bending element are disposed adjacent to each other in the longitudinal axis direction and the wire is disposed in both of the first and second wire accommodating grooves.

An endoscope according to an aspect of the present invention includes an endoscope bending portion including a plurality of bending elements connected in a longitudinal axis direction, the endoscope bending portion being enabled to bend in two bending directions by pulling a wire. Each of the plurality of bending elements includes an opening formed on an outer surface in the longitudinal axis direction, a first bending element including a first wire accommodating groove continuous with the opening and formed at a first position crossing the bending direction at 45 degrees to 135 degrees, and a second bending element including a second wire accommodating groove continuous with the opening and formed at a second position crossing the bending direction at 225 degrees to 315 degrees. The first bending element and the second bending element are disposed adjacent to each other in the longitudinal axis direction and the wire is disposed in both of the first and second wire accommodating grooves.

DETAILED DESCRIPTION OF THE PREFERRED EMBODIMENTS

Figure 2:
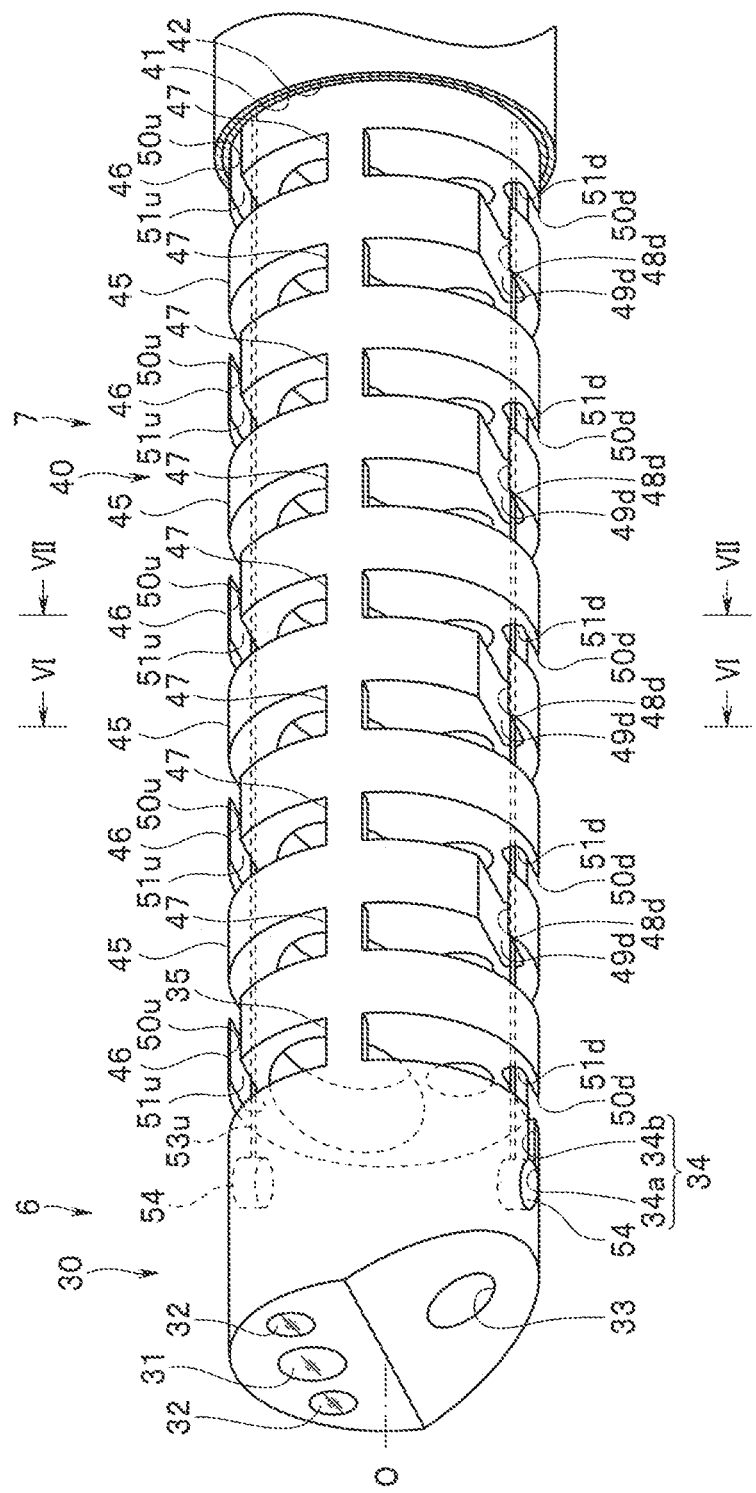
FIG. 2 is a perspective view of a bending portion and a distal end portion shown by removing part of a sheath and a braid.
Figure 3:
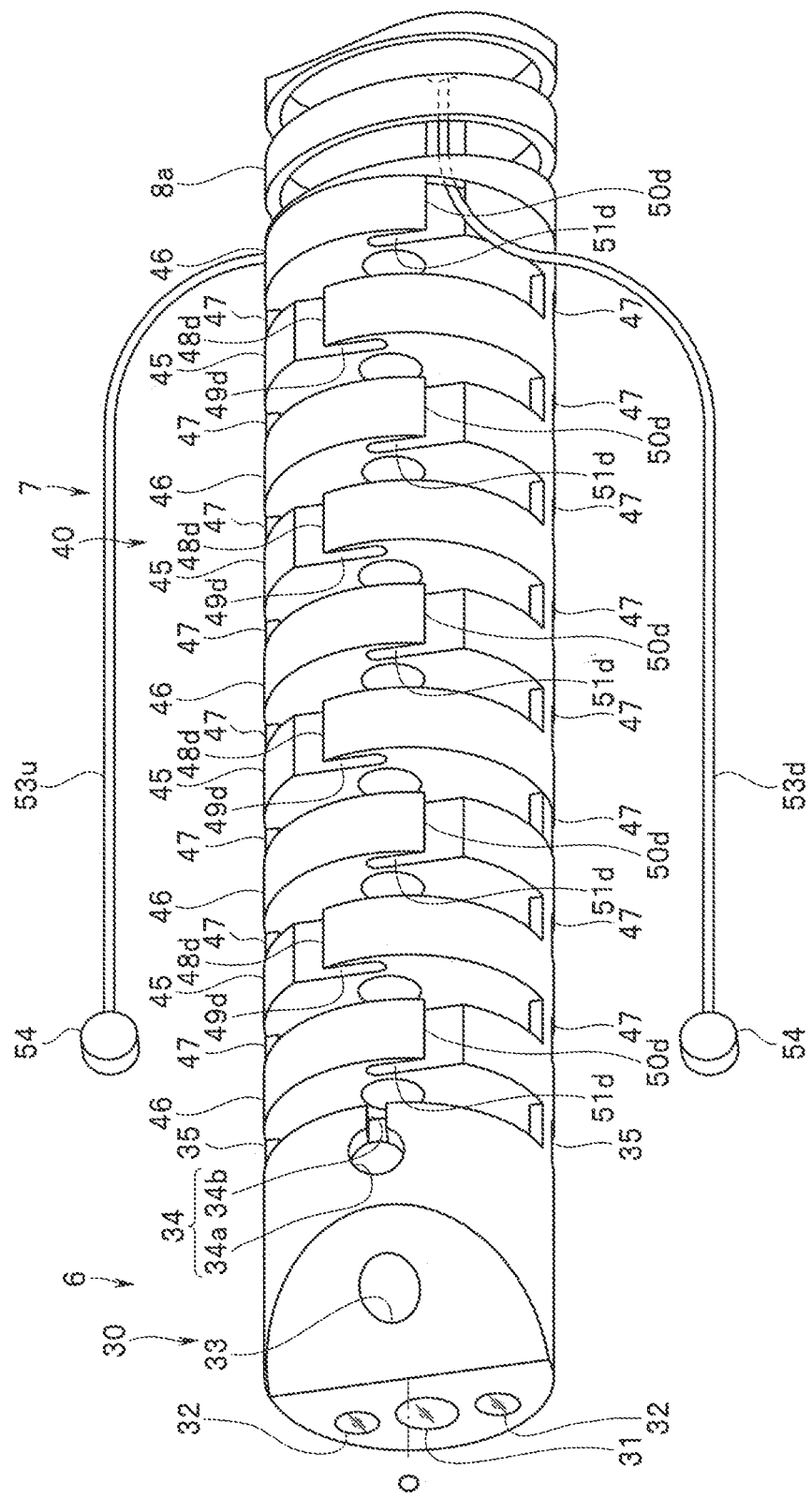
FIG. 3 is a perspective view illustrating a bending tube before mounting a pulling wire.
Figure 4:
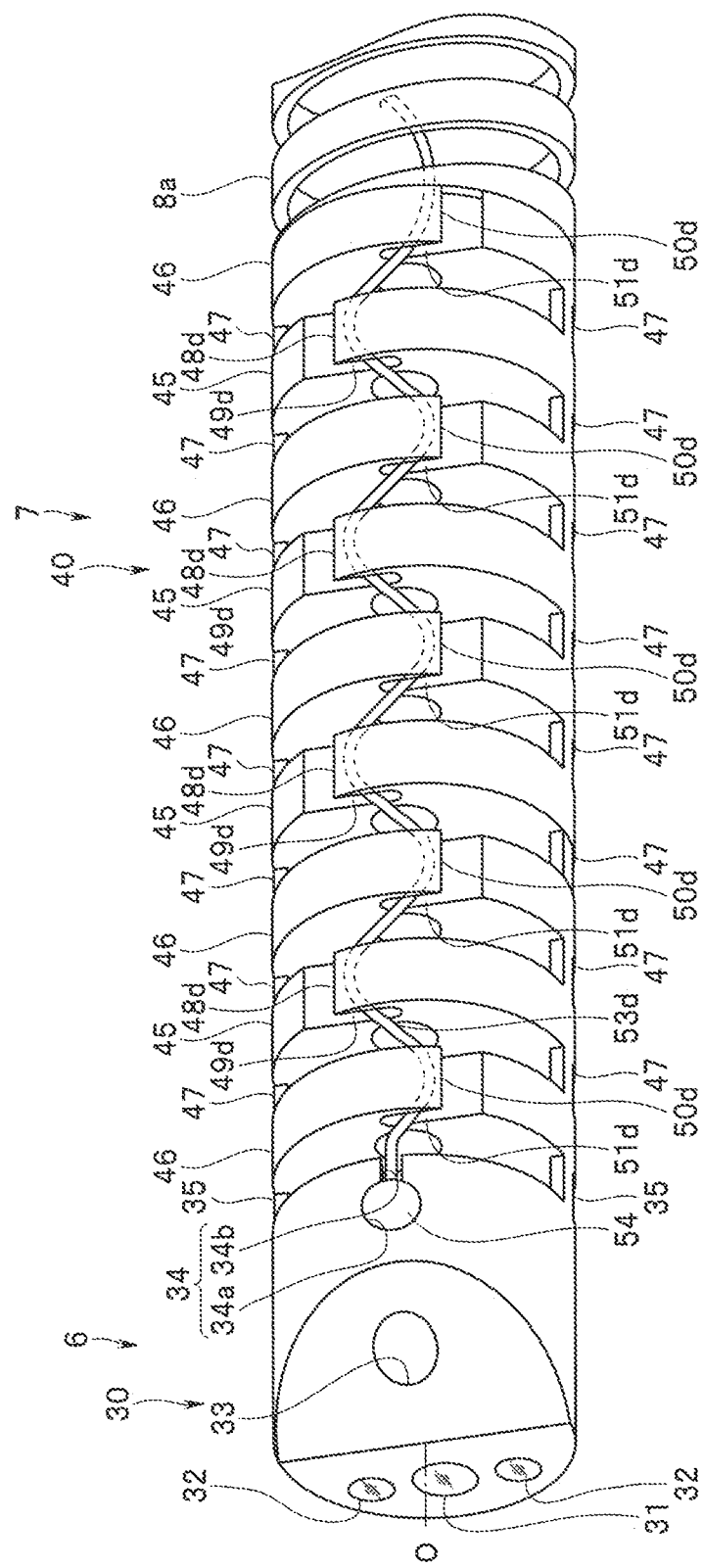
FIG. 4 is a perspective view illustrating the bending tube during mounting of the pulling wire.
Figure 5:
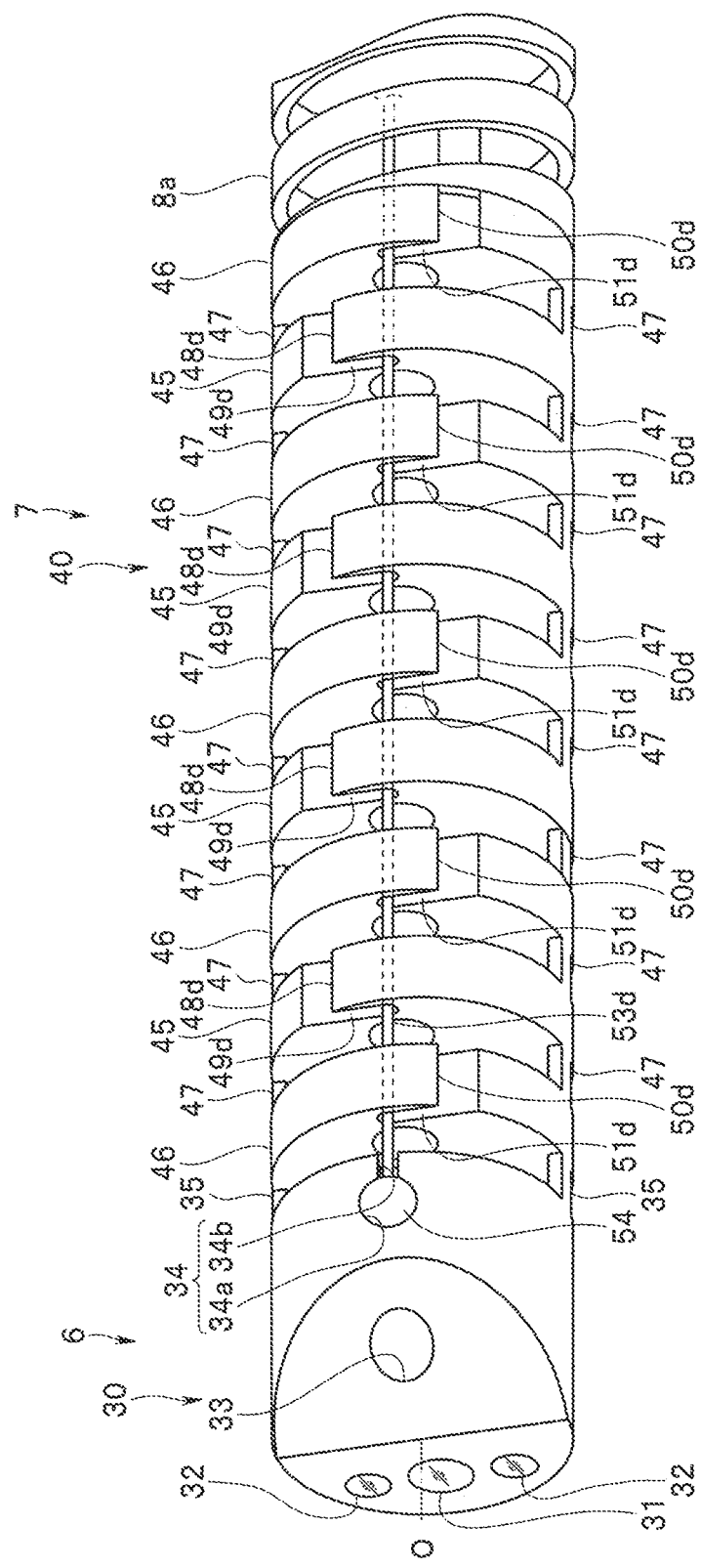
FIG. 5 is a perspective view illustrating the bending tube after mounting of the pulling wire.
Figure 6:
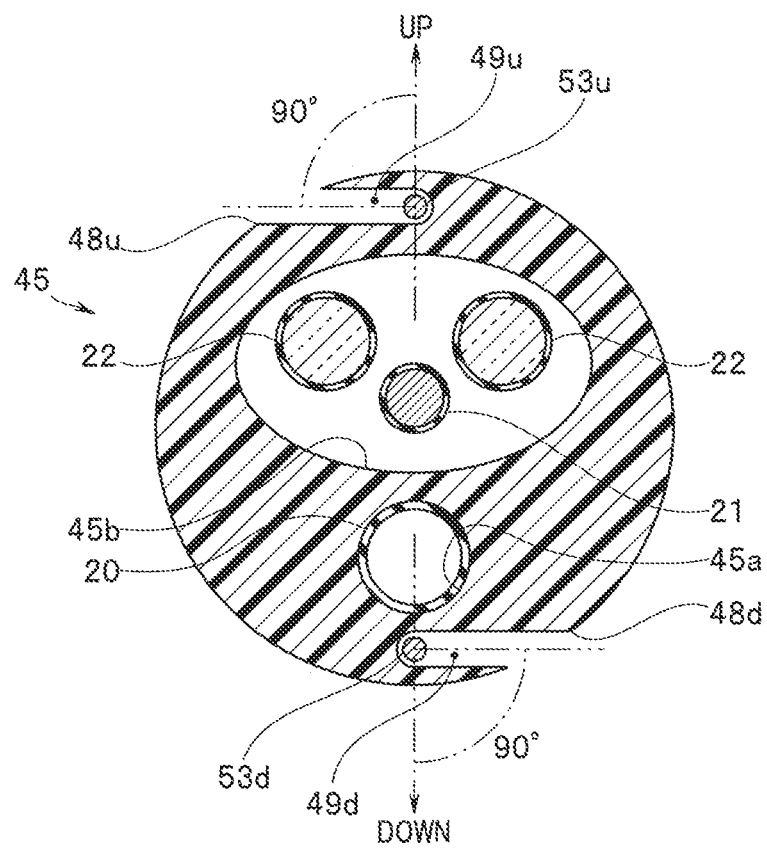
FIG. 6 is a VI-VI cross-sectional view of FIG. 2.
Figure 7:
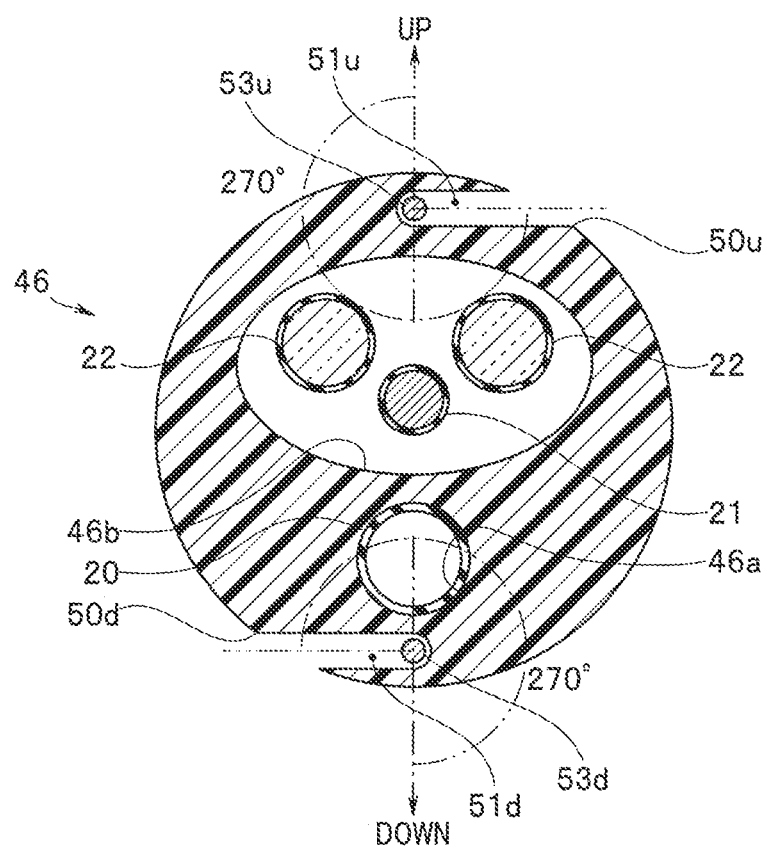
FIG. 7 is a VII-VII cross-sectional view of FIG. 2.
Figure 8:
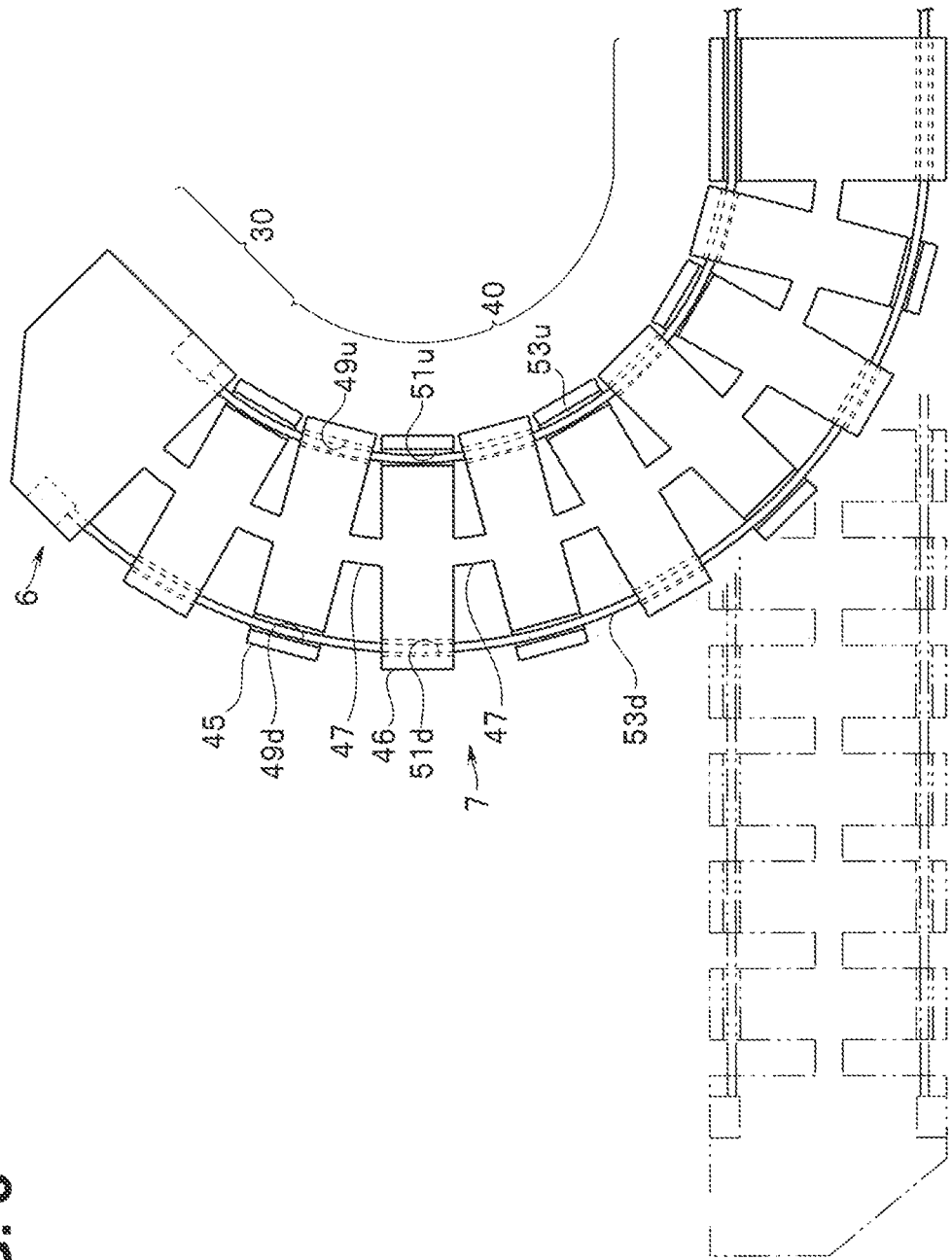
FIG. 8 is an explanatory diagram illustrating a bending condition of the bending tube.

Hereinafter, an embodiment of the present invention will be described with reference to the accompanying drawings. The drawings relate to an embodiment of the present invention, in which FIG. 1 is an external perspective view of an endoscope, FIG. 2 is a perspective view of a bending portion and a distal end portion shown by removing part of a sheath and a braid, FIG. 3 is a perspective view illustrating a bending tube before mounting a pulling wire, FIG. 4 is a perspective view illustrating the bending tube during mounting of the pulling wire, FIG. 5 is a perspective view illustrating the bending tube after mounting of the pulling wire, FIG. 6 is a VI-VI cross-sectional view of FIG. 2, FIG. 7 is a VII-VII cross-sectional view of FIG. 2, and FIG. 8 is an explanatory diagram illustrating a bending condition of the bending tube.

Figure 1:
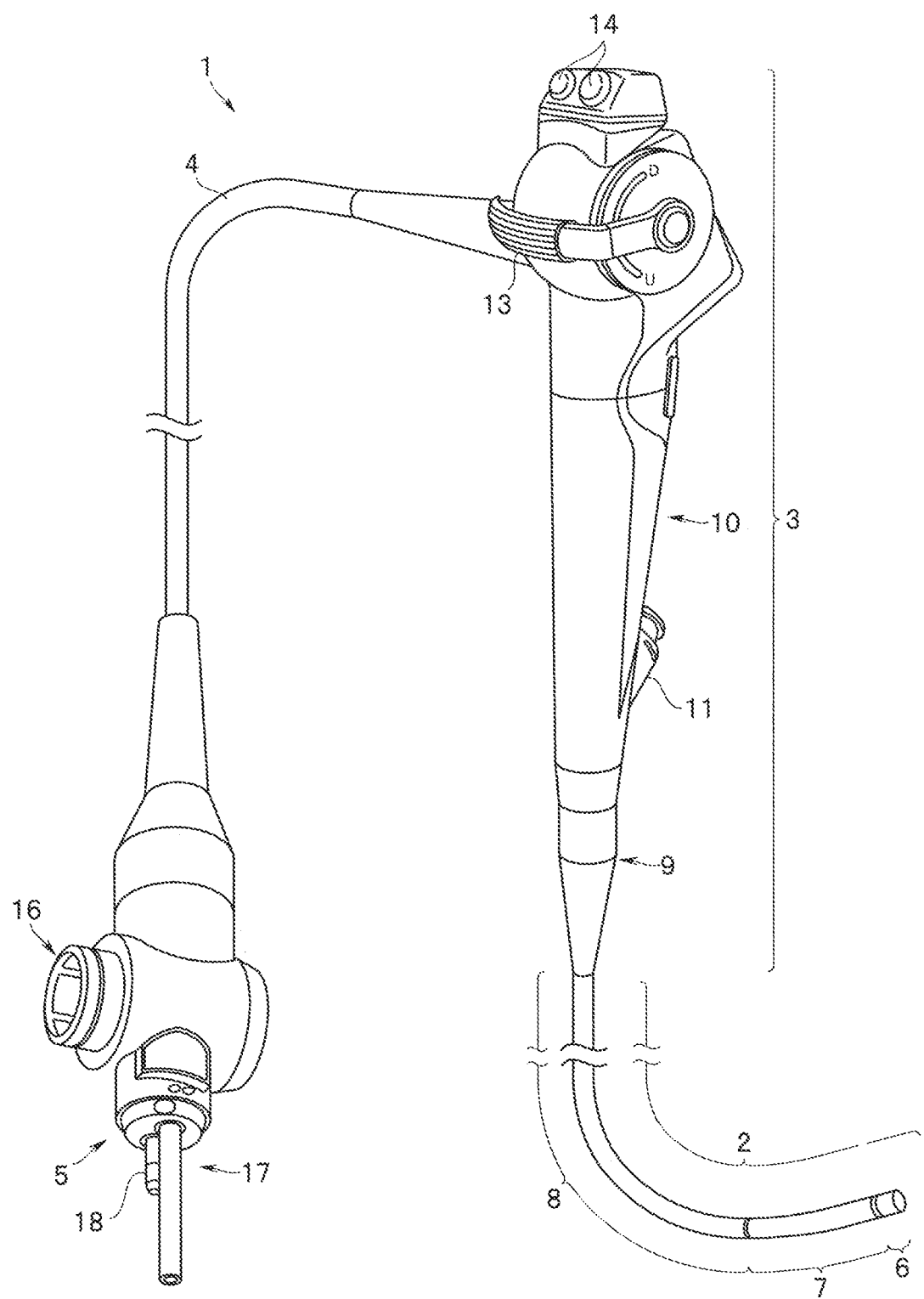
FIG. 1 is an external perspective view of an endoscope.

An endoscope 1 shown in FIG. 1 is constructed of an elongated (long) insertion portion 2 inserted into a body cavity of a subject, an operation portion 3 connected to a proximal end of the insertion portion 2, a universal cable 4 extending from a proximal end of the operation portion 3 and an endoscope connector 5 disposed at an extending end of the universal cable 4.

The insertion portion 2 is a flexible tubular member with a distal end portion 6, a bending portion 7 and a flexible tube portion 8 connected in a row from a distal end side. Of these portions, the distal end portion 6 accommodates/disposes an image pickup unit (not shown) incorporating an image pickup device and an illumination optical system unit or the like.

Note that the endoscope 1 is not limited to an electronic endoscope provided with an image pickup unit at the distal end portion 6, and may also be a fiber scope with an image guide fiber disposed at the insertion portion 2.

The bending portion 7 is a mechanical region configured to be able to actively bend in two bending directions (UP-DOWN): up and down directions. Note that in the present embodiment, up-down and left-right directions of the insertion portion 2 or the like are defined for convenience in association with up-down and left-right directions of an endoscopic image picked up by the image pickup unit.

The flexible tube portion 8 is a tubular member with flexibility configured to be passively flexible. In addition to a treatment instrument insertion channel 20, various signal cables 21 extending from the image pickup unit or the like and a light guide bundle 22 or the like optically connected to an illumination optical system unit are inserted through the flexible tube portion 8.

The operation portion 3 is constructed of a bend preventing portion 9 connected to the flexible tube portion by covering the proximal end of the flexible tube portion 8 provided on a distal end side and a grasping portion 10 connected to the bend preventing portion 9 and graspable by the user's hand.

A treatment instrument insertion portion 11 communicating with a proximal end side of the treatment instrument insertion channel 20 is provided on a distal end side of the grasping portion 10. An operation lever 13 to perform bending operation of the bending portion 7 and operation switches 14 to which various functions of the endoscope 1 are assigned are provided on a proximal end side of the grasping portion 10.

The universal cable 4 is a composite cable configured to allow, for example, the various signal cables 21 extending from the distal end portion 6 of the insertion portion 2 and the light guide bundle 22 (see FIGS. 6 and 7) to be inserted through the inside of the universal cable 4 and allow an air/water feeding tube (not shown) or the like, a distal end side of which is connected to the treatment instrument insertion channel 20, to be inserted through the inside of the universal cable 4.

The endoscope connector 5 is constructed of an electric connector unit 16 to connect the various signal cables 21 to a video processor (not shown), which is an external device, a light source connector unit 17 to connect the light guide bundle 22 to a light source device (not shown), which is an external device, and an air/water feeding plug 18 to connect an air/water feeding tube to an air/water feeding device (not shown), which is an external device.

Next, a configuration of the distal end portion of the insertion portion 2 of the endoscope 1 according to the present embodiment will be described with reference to FIG. 2 to FIG. 8.

The distal end portion 6 of the insertion portion 2 includes a distal end rigid portion 30, which is a substantially columnar rigid frame formed of resin or the like. An observation window 31 formed of a distal end face of the image pickup unit, two illumination windows 32 formed of a distal end face of an illumination optical system unit, and a channel opening 33 with which the distal end side of the treatment instrument insertion channel 20 communicates are disposed on the distal end face of the distal end rigid portion 30.

A pair of upper and lower wire stoppers 34 are provided near a proximal end of a circumferential portion of the distal end rigid portion 30 (only a lower-side wire stopper 34 is illustrated in FIG. 2 to FIG. 5). The wire stoppers 34 are constructed of bottomed hole portions 34a opened at a top or at a bottom and a groove portion 34b configured to allow the hole portions 34a to communicate with the proximal end of the distal end rigid portion 30.

As illustrated in FIGS. 2 and 3, the bending portion 7 is constructed of a bending tube 40, a braid 41 configured to cover an outer circumference of the bending tube 40 and a sheath 42 configured to cover an outer circumference of the braid 41.

The bending tube 40 is constructed of a plurality of bending pieces as bending elements connected in an insertion axis O direction. In the present embodiment, more specifically, the bending tube 40 is constructed of a plurality of first bending pieces 45 as first bending elements and a plurality of second bending pieces 46 as second bending elements.

In the present embodiment, the first bending pieces 45 and the second bending pieces 46 are alternately arrayed along the insertion axis O direction. The first bending piece 45 and the second bending piece 46 adjacent to each other are connected together via a pair of left and right connection members 47.

Note that the bending tube 40 of the present embodiment is integrally formed by resin molding. Furthermore, the bending tube 40 of the present embodiment is also formed integrally with the distal end rigid portion 30, and a bending piece located at a distalmost of the bending tube 40 (second bending piece 46 in the illustrated example) is connected to the distal end rigid portion 30 by a pair of left and right connection members 35.

As illustrated in FIG. 2 to FIG. 6, the first bending piece 45 has a substantially columnar shape with a flat external shape. A first insertion hole 45a and a second insertion hole 45b penetrating in an insertion axis direction are formed inside the first bending piece 45. The treatment instrument insertion channel 20 is inserted through the first insertion hole 45a and internal components such as the signal cables 21 and the light guide bundle 22 are inserted through the second insertion hole 45b.

A first upper-side opening 48u and a first lower-side opening 48d are provided as a pair of openings extending in a longitudinal axis (insertion axis O) direction from a distal end to a proximal end of the first bending piece 45 on an upper side and a lower side of an outer surface of the first bending piece 45.

The first upper-side opening 48u of the present embodiment is disposed at a position near the upper left side of the first bending piece 45 (first position).

A first upper-side wire accommodating groove 49u as a wire accommodating groove is continuous with the first upper-side opening 48u. The first upper-side wire accommodating groove 49u is formed so that the depth direction of the first upper-side wire accommodating groove 49u extends in a direction crossing an up direction, which is a bending direction of the bending portion 7 (bending tube 40) at an angle of 90 degrees.

The first upper-side wire accommodating groove 49u is a groove to accommodate the pulling wire 53u to bend mainly the bending portion 7 toward the upper side. It is possible to insert the pulling wire 53u through the first upper-side wire accommodating groove 49u via the first upper-side opening 48u from outside of the bending tube 40 (first bending piece 45).

The first lower-side opening 48d is disposed at a position near the lower right side of the first bending piece 45 (first position). More specifically, the first lower-side opening 48d is disposed at a rotationally symmetrical position of 180 degrees to the first upper-side opening 48u with respect to a center of the first bending piece 45.

A first lower-side wire accommodating groove 49d is continuous with the first lower-side opening 48d as a wire accommodating groove. The first lower-side wire accommodating groove 49d is formed so that the depth direction of the first lower-side wire accommodating groove 49d extends in a direction crossing a down direction, which is a bending direction of the bending portion 7 (bending tube 40) at an angle of 90 degrees.

The first lower-side wire accommodating groove 49d is a groove to accommodate the pulling wire 53d to cause the bending portion 7 mainly to bend downward. The pulling wire 53d can be inserted into the first lower-side wire accommodating groove 49d from an outside of the bending tube 40 (first bending piece 45) via the first lower-side opening 48d.

The second bending piece 46 has a substantially columnar shape with a flat external shape. A first insertion hole 46a and a second insertion hole 46b penetrating in the insertion axis direction are formed inside the second bending piece 46. The treatment instrument insertion channel 20 is inserted through the first insertion hole 46a and the various signal cables 21 and internal components such as the light guide bundle 22 are inserted through the second insertion hole 46b.

On an upper side and a lower side of the outer surface of the second bending piece 46, a second upper-side opening 50u and a second lower-side opening 50d are provided as a pair of openings extending from a distal end to a proximal end of the second bending piece 46 in the longitudinal axis (insertion axis O) direction.

The second upper-side opening 50u of the present embodiment is disposed at a position near the upper right side of the second bending piece 46 (second position).

A second upper-side wire accommodating groove 51u as a wire accommodating groove is continuous with the second upper-side opening 50u. The second upper-side wire accommodating groove Mu is formed so that a depth direction of the second upper-side wire accommodating groove 51u extends in a direction crossing the up direction, which is a bending direction of the bending portion 7 (bending tube 40), at an angle of 270 degrees.

In this case, an extending end portion of the second upper-side wire accommodating groove 51u is formed so as to overlap an extending end portion of the first upper-side wire accommodating groove 49u in the insertion axis O direction.

The second upper-side wire accommodating groove 51u is a groove to accommodate the pulling wire 53u to cause the bending portion 7 mainly to bend upward. The pulling wire 53u can be inserted through the second upper-side wire accommodating groove 51u from an outside of the bending tube 40 (second bending piece 46) via the second upper-side opening 50u.

The second lower-side opening 50d is disposed at a position near the lower side of the second bending piece 46 (second position). More specifically, the second lower-side opening 50d is disposed at a rotationally symmetrical position of 180 degrees to the second upper-side opening 50u with respect to the center of the second bending piece 46.

A second lower-side wire accommodating groove 51d as a wire accommodating groove is continuous with the second lower-side opening 50d. The second lower-side wire accommodating groove 51d is formed so that the depth direction of the second lower-side wire accommodating groove 51d extends in a direction crossing the down direction, which is the bending direction of the bending portion 7 (bending tube 40).

In this case, an extending end portion of the second lower-side wire accommodating groove 51d is formed so as to overlap an extending end portion of the first lower-side wire accommodating groove 49d in the insertion axis O direction.

The second lower-side wire accommodating groove 51d is a groove to accommodate the pulling wire 53d to cause the bending portion 7 mainly to bend downward. The pulling wire 53d can be inserted through the second lower-side wire accommodating groove 51d from an outside of the bending tube 40 (second bending piece 46) via the second lower-side opening 50d.

The pulling wires 53u and 53d can be inserted through the bending tube 40 configured in this manner, for example, in a step after assembling the bending tube 40 to a coiled tube 8a constituting the flexible tube portion 8 and before covering the bending tube 40 with the braid 41 and the sheath 42.

In other words, as illustrated, for example, in FIG. 3, when connecting the bending tube 40 to the coiled tube 8a, the operator, or the like, causes the distal end sides of the pulling wires 53u and 53d to extend to an outside of the bending tube 40 via the opening and the wire accommodating groove of the bending piece located at a proximalmost. Here, in the illustrated example, the second bending piece 46 is disposed at the proximalmost of the bending tube 40.

Therefore, the pulling wire 53u is caused to extend to the outside of the bending tube 40 via the second upper-side opening 50u and the second upper-side wire accommodating groove 51u of the second bending piece 46, and the pulling wire 53d is caused to extend to the outside of the bending tube 40 via the second lower-side opening 50d and the second lower-side wire accommodating groove 51d.

Note that as illustrated in the drawing, substantially disk-shaped locking members 54 that can be accommodated inside the wire stoppers 34 of the distal end rigid portion 30 are provided at the distal ends of the pulling wires 53u and 53d.

As illustrated, for example, in FIG. 4, the operator, or the like, causes the pulling wire 53u to meander so as to be accommodated sequentially from the proximal end side with respect to each first upper-side wire accommodating groove 49u and each second upper-side wire accommodating groove 51u, and cause the pulling wire 53d to meander so as to be accommodated sequentially from the proximal end side with respect to each first lower-side wire accommodating groove 49d and each second lower-side wire accommodating groove 51d. In this way, the respective pulling wires 53u and 53d are inserted through the bending tube 40.

After that, the operator, or the like, accommodates the locking members 54 provided at the distal ends of the respective pulling wires 53u and 53d to insides of the corresponding wire stoppers 34 and fixes the locking members 54 by bonding or the like. As a result, insertion states of the respective pulling wires 53u and 53d are maintained.

After that, the operator, or the like, pulls the respective pulling wires 53u and 53d from the operation portion 3 side. For example, as illustrated in FIG. 5, routing positions of the respective pulling wires 53u and 53d inside the bending tube 40 are automatically adjusted to appropriate positions so as to be substantially parallel to the insertion axis O.

In other words, at the top of the bending tube 40 of the present embodiment, the first upper-side opening 48u provided in the first bending piece 45 and the second upper-side opening 50u provided in the second bending piece 46 are disposed in opposite directions.

The first upper-side wire accommodating groove 49u continuous with the first upper-side opening 48u and the second upper-side wire accommodating groove 51u continuous with the second upper-side opening 50u extend in directions in which their respective extending end portions overlap.

Therefore, when the pulling wire 53u is pulled, the first upper-side wire accommodating groove 49u and the second upper-side wire accommodating groove 51u guide the pulling wire 53u toward their respective extending end portions.

As a result, the routing position of the pulling wire 53u in the bending tube 40 is automatically adjusted (self-aligned) to an appropriate position.

Similarly, at the bottom of the bending tube 40 of the present embodiment, the first lower-side opening 48d provided in the first bending piece 45 and the second lower-side opening 50d provided in the second bending piece 46 are disposed in opposite directions.

The first lower-side wire accommodating groove 49d continuous with the first lower-side opening 48d and the second lower-side wire accommodating groove 51d continuous with the second lower-side opening 50d extend in directions in which their respective extending end portions overlap.

Therefore, when the pulling wire 53d is pulled, the first lower-side wire accommodating groove 49d and the second lower-side wire accommodating groove 51d guide the pulling wire 53d toward their respective extending end portions.

As a result, the routing position of the pulling wire 53d in the bending tube 40 is automatically adjusted (self-aligned) to an appropriate position.

Furthermore, since the first upper-side wire accommodating groove 49u and the second upper-side wire accommodating groove 51u are disposed so that the bag-shaped extending end portions overlap, movements in a direction in which the pulling wire 53u will slip off are restricted. Similarly, since the first lower-side wire accommodating groove 49d and the second lower-side wire accommodating groove 51d are disposed so that the bag-shaped extending end portions overlap, movements in a direction in which the pulling wire 53d will slip off are restricted.

Note that since the bending tube 40 to which the pulling wires 53u and 53d have been attached is covered with the braid 41 and the sheath 42, the braid 41 and the sheath 42 more reliably restrict the pulling wires 53u and 53d from moving in directions in which the pulling wires 53u and 53d will slip off.

Through these operations, as illustrated, for example, in FIG. 8 when the pulling wires 53u and 53d are pulled or relaxed in conjunction with operation on the operation lever 13, the pulling wire 53u is held inside the first and second upper-side wire accommodating grooves 49u and 51u and the pulling wire 53d is held inside the first and second lower-side wire accommodating grooves 49d and 51d, and the bending tube 40 (bending portion 7) is reliably bent.

According to such an embodiment, the bending tube 40 is constructed of the first bending piece 45 including the first upper-side opening 48u and the first lower-side opening 48d formed on the outer surface in the longitudinal axis O direction, and the first upper-side wire accommodating groove 49u and the first lower-side wire accommodating groove 49d continuous with the first upper-side opening 48u and the first lower-side opening 48d respectively and formed in a direction crossing the two up and down bending directions at an angle of 90 degrees, and the second bending piece 46 including the second upper-side opening 50u and the second lower-side opening 50d formed on the outer surface in the longitudinal axis O direction, and the second upper-side wire accommodating groove 51u and the second lower-side wire accommodating groove 51d continuous with the second upper-side opening 50u and the second lower-side opening 50d respectively and formed in a direction crossing the two up and down bending directions at an angle of 90 degrees, and it is thereby possible to insert the pulling wire 53u into the first upper-side wire accommodating groove 49u and the second upper-side wire accommodating groove 51u from the outside of the bending tube 40 and insert the pulling wire 53d into the first lower-side wire accommodating groove 49d and the second lower-side wire accommodating groove 51d from the outside of the bending tube 40, and thereby attach the pulling wires 53u and 53d to the bending tube 40 by a simple operation.

In other words, it is possible to insert the pulling wires 53u and 53d through the bending tube 40 by a simple operation only from the outside of the bending tube 40 without the need to perform minute operation inside the bending tube 40.

In this case, by disposing the first upper-side wire accommodating groove 49u and the second upper-side wire accommodating groove 51u at symmetrical positions with respect to the center of the bending direction on the upper side (or more specifically, symmetrical projection positions), it is possible to automatically adjust the pulling wire 53u inserted through the first upper-side wire accommodating groove 49u and the second upper-side wire accommodating groove 51u to appropriate positions substantially parallel to the insertion axis O, and reliably prevent the inserted pulling wire 53u from slipping off.

Similarly, by disposing the first lower-side wire accommodating groove 49d and the second lower-side wire accommodating groove 51d at symmetrical positions with respect to the center of the bending direction on the lower side (or more specifically, symmetrical projection positions), it is possible to automatically adjust the pulling wire 53d inserted through the first lower-side wire accommodating groove 49d and the second lower-side wire accommodating groove 51d to appropriate positions substantially parallel to the insertion axis O, and reliably prevent the inserted pulling wire 53d from slipping off.

Here, the first and second upper-side wire accommodating grooves 49u and 51u and the first and second lower-side wire accommodating grooves 49d and 51d are not limited to the angles of the aforementioned embodiment, but may be caused to cross the respective up and down bending directions of the bending portion 7 at angles ranging from 45 degrees to 135 degrees or 225 degrees to 315 degrees.

Figure 9:
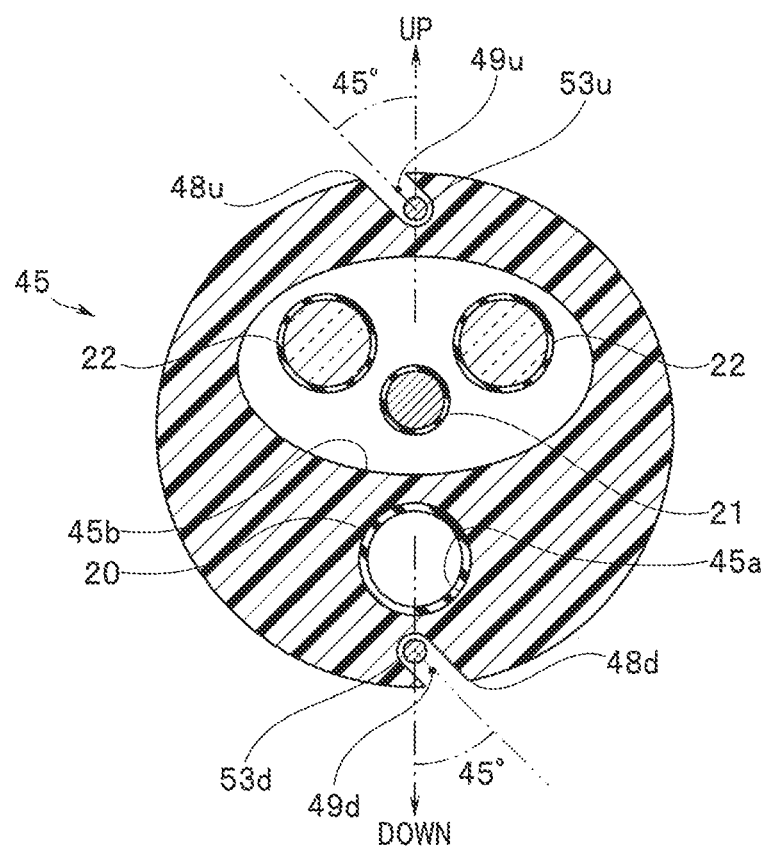
FIG. 9 relates to a first modification and is a cross-sectional view of main parts of a first bending piece of a bending portion shown by removing the sheath and the braid.
Figure 10:
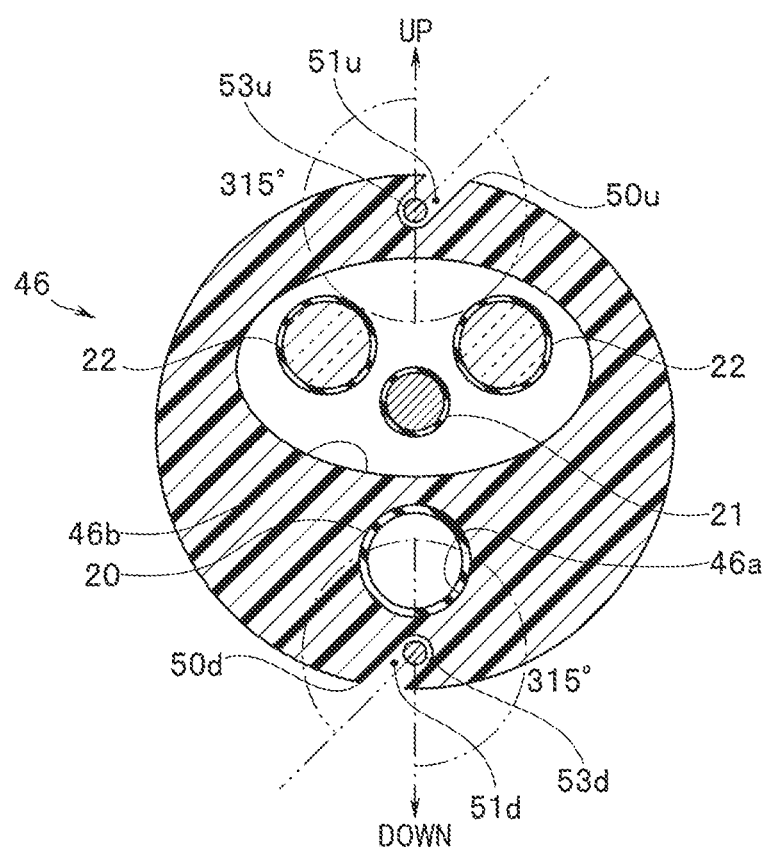
FIG. 10 relates to the first modification and is a cross-sectional view of main parts of a second bending piece of a bending portion shown by removing the sheath and the braid.

For example, as illustrated in FIGS. 9 and 10, it is also possible to cause the first upper-side wire accommodating groove 49u and the first lower-side wire accommodating groove 49d to cross the up and down bending directions at 45 degrees and cause the second upper-side wire accommodating groove 51u and the second lower-side wire accommodating groove 51d to cross the up and down bending directions at 315 degrees. In this way, by causing the first upper-side wire accommodating groove 49u and the first lower-side wire accommodating groove 49d to cross the up and down bending directions at angles smaller than 90 degrees and causing the second upper-side wire accommodating groove 51u and the second lower-side wire accommodating groove 51d to cross the up and down bending directions at angles greater than 270 degrees, it is possible to reduce the interval between the first upper-side opening 48u and the second upper-side opening 50u and the interval between the first lower-side opening 48d and the second lower-side opening 50d. Therefore, it is possible to reduce the meandering width when attaching the pulling wires 53u and 53d to the bending tube 40 and further improve workability.

Figure 11:
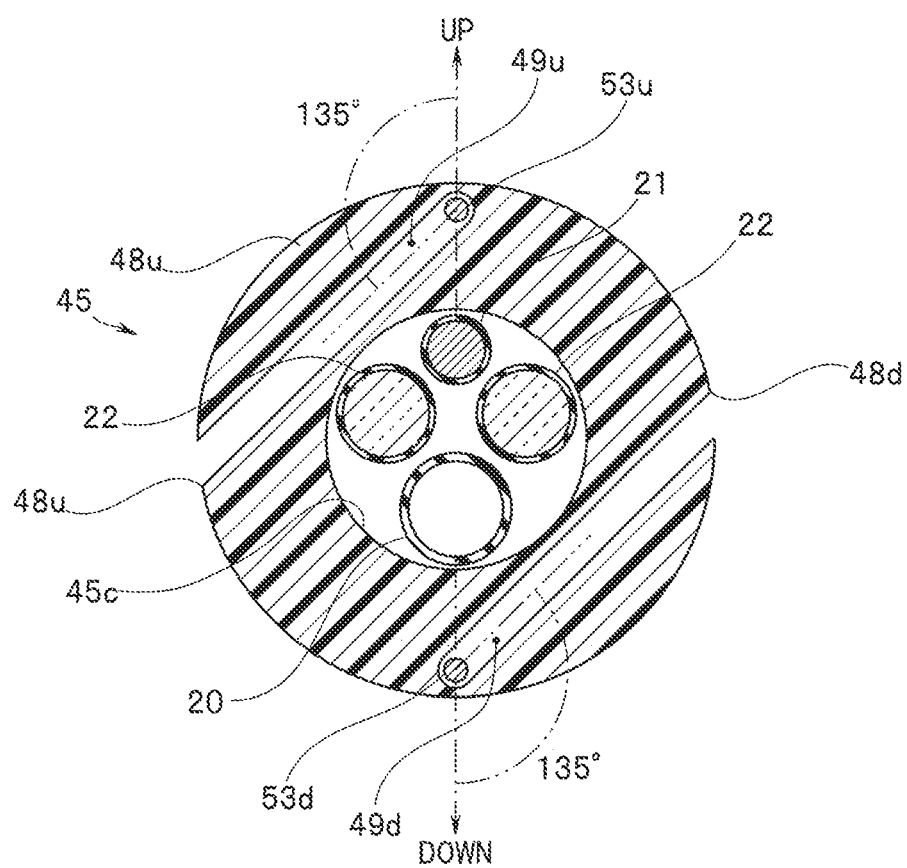
FIG. 11 relates to a second modification and is a cross-sectional view of main parts of the first bending piece of the bending portion shown by removing the sheath and the braid.
Figure 12:
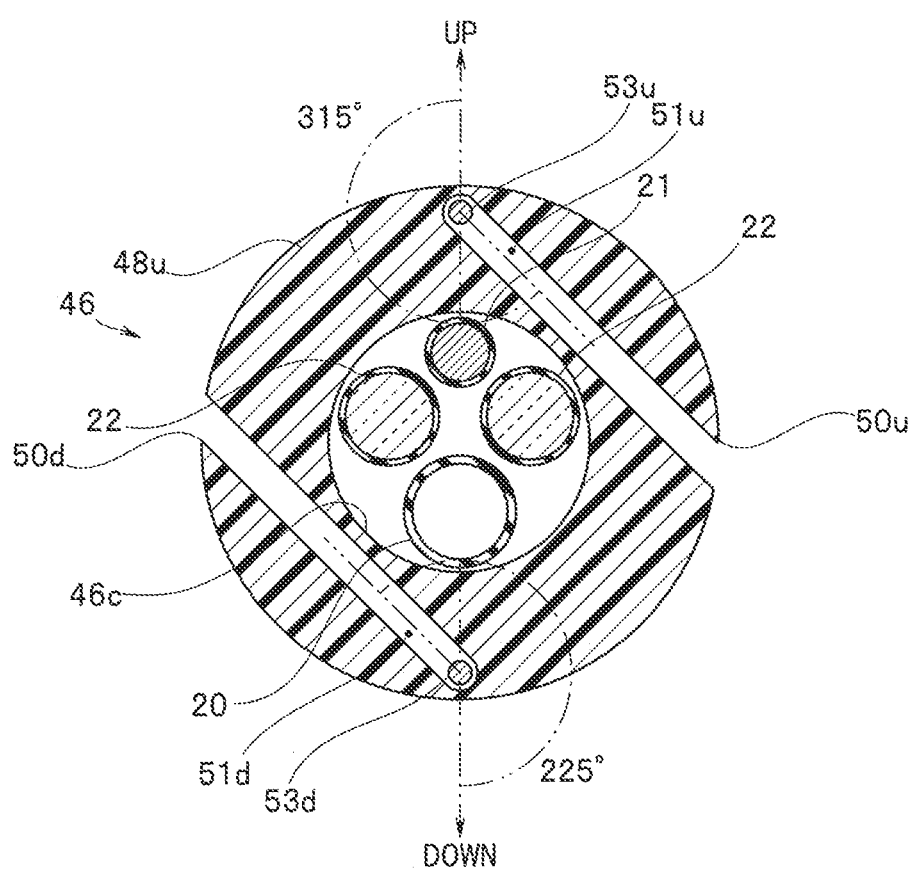
FIG. 12 relates to the second modification and is a cross-sectional view of main parts of a second bending piece of the bending portion shown by removing the sheath and the braid.

Alternatively, as illustrated, for example, in FIGS. 11 and 12, it is also possible to cause the first upper-side wire accommodating groove 49u and the first lower-side wire accommodating groove 49d to cross the up and down bending directions at 135 degrees respectively and cause the second upper-side wire accommodating groove 51u and the second lower-side wire accommodating groove 51d to cross the up and down bending directions at 225 degrees respectively. Note that FIGS. 11 and 12 illustrate configuration examples of the first and second bending pieces 45 and 46 where single insertion holes 45c and 46c are formed inside respectively. Thus, by causing the first upper-side wire accommodating groove 49u and the first lower-side wire accommodating groove 49d to cross the up and down bending directions at angles greater than 90 degrees and causing the second upper-side wire accommodating groove 51u and the second lower-side wire accommodating groove 51d to cross the up and down bending directions at angles smaller than 270 degrees, it is possible to more reliably prevent the pulling wires 53u and 53d from slipping off.

The first bending piece 45 and the second bending piece 46 are not limited to the arrangement of the aforementioned embodiment, but may be configured in any combined arrangement.

Figure 13:
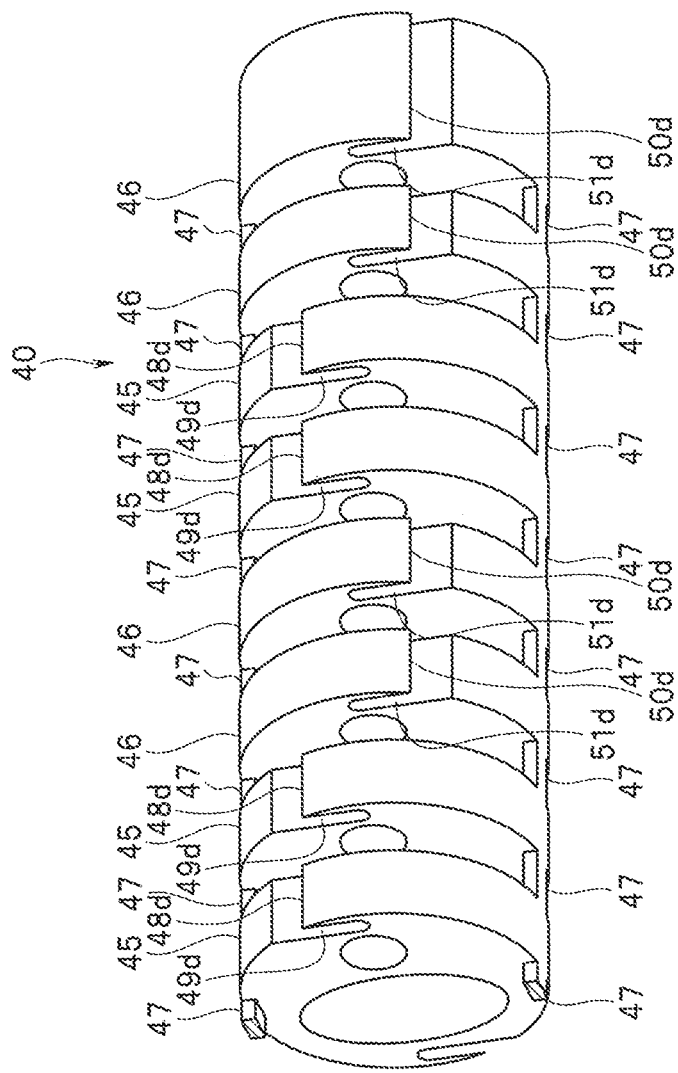
FIG. 13 relates to a third modification and is a perspective view of a bending tube.

As illustrated, for example, in FIG. 13, it is also possible to alternately dispose a plurality of the first bending pieces 45 and the second bending pieces 46 (e.g., two pieces each) in the insertion axis O direction. Such a configuration makes it possible to reduce the number of times of the pulling wires 53u and 53d being caused to meander when the pulling wires 53u and 53d are attached to the bending tube 40, and make workability more convenient.

Figure 14:
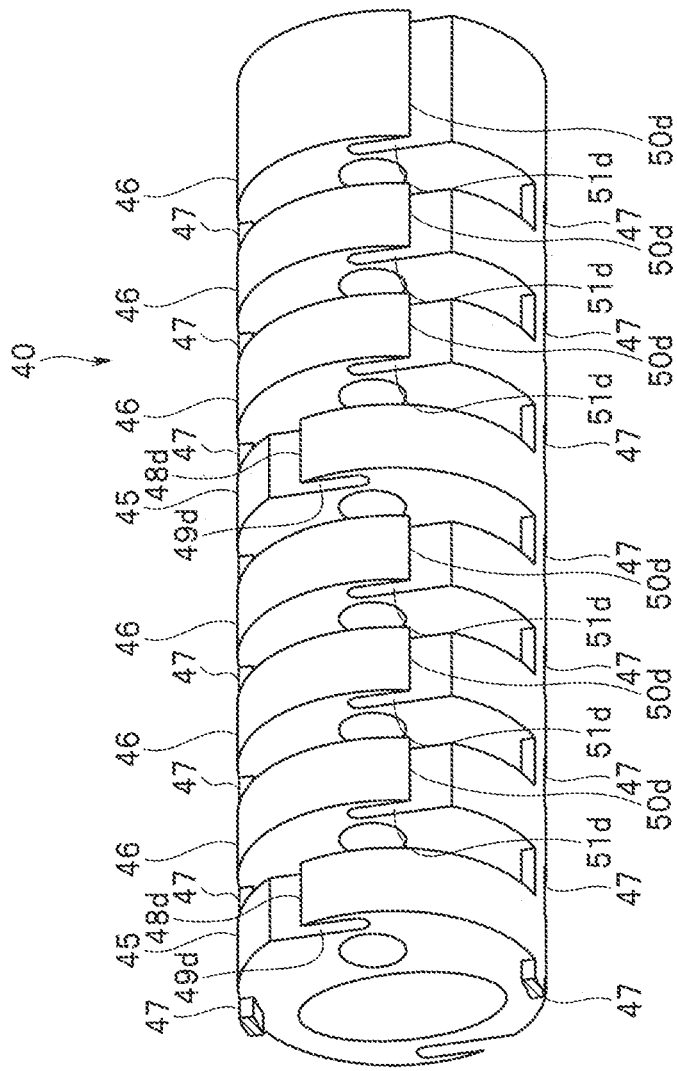
FIG. 14 relates to a fourth modification and is a perspective view of a bending tube.

Alternatively, as illustrated, for example, in FIG. 14, it is also possible to dispose one first bending piece 45 every time a plurality of (e.g., 3) second bending pieces 46 are disposed along the insertion axis O direction. Such a configuration makes it possible to reduce the number of times of the pulling wires 53u and 53d being caused to meander when the pulling wires 53u and 53d are attached to the bending tube 40, and make workability more convenient.

The bending direction of the bending tube 40 is not limited to only two up and down directions, but may be two left and right directions or one of up, down, left and right directions.

Figure 15:
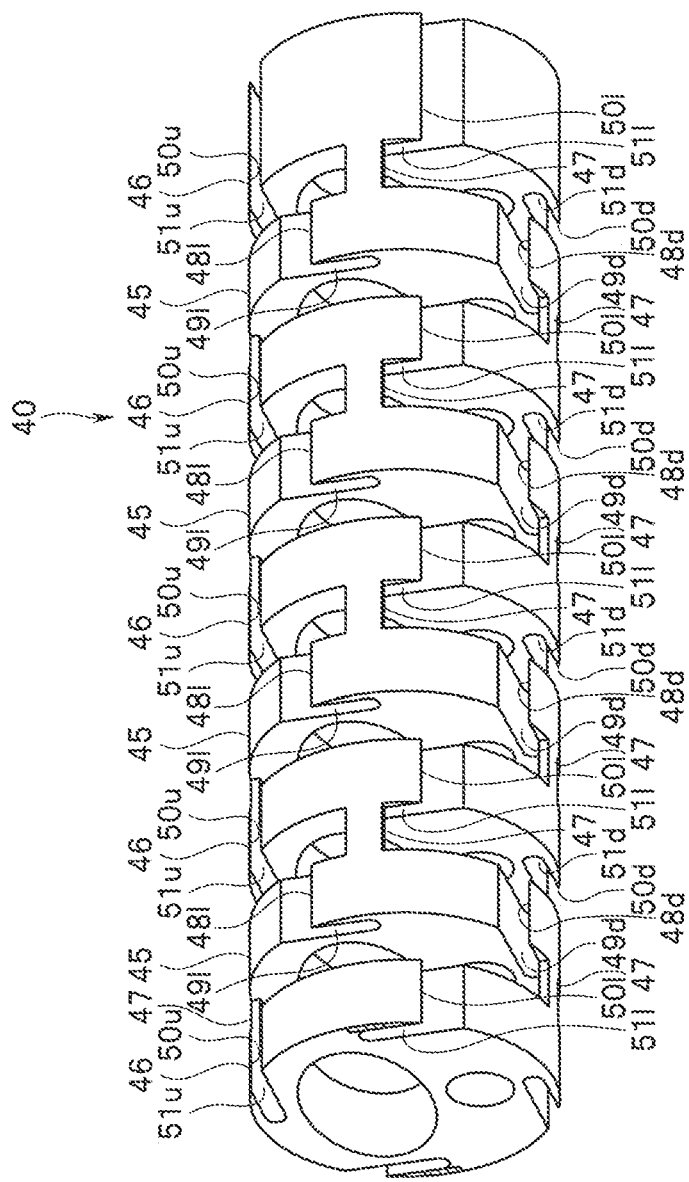
FIG. 15 relates to a fifth modification and is a perspective view of a bending tube.

Furthermore, as illustrated, for example, in FIG. 15, the bending direction of the bending tube 40 may be four up, down, left and right directions.

Figure 16:
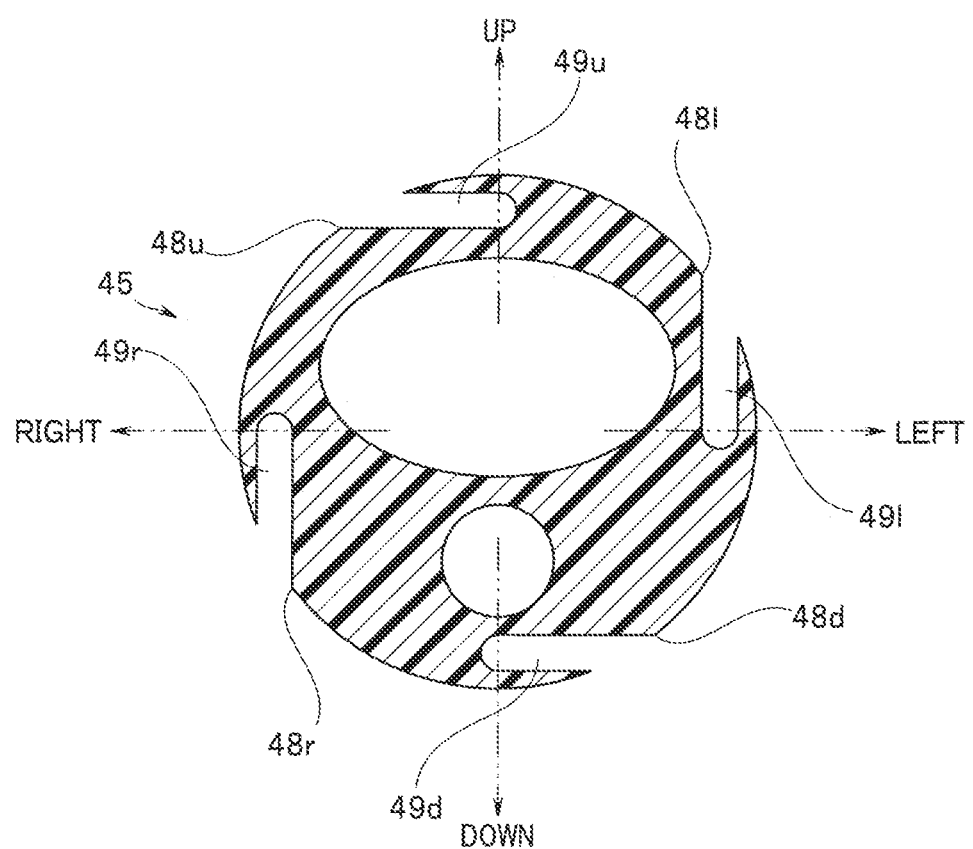
FIG. 16 relates to the fifth modification and is a cross-sectional view of main parts of the first bending piece of the bending portion shown by removing the sheath and the braid.

In this case, as illustrated, for example, in FIG. 16, the first bending piece 45 is provided with not only the first upper-side wire accommodating groove 49u continuous with the first upper-side opening 48u and the first lower-side wire accommodating groove 49d continuous with the first lower-side opening 48d, but also a first left-side wire accommodating groove 49l continuous with a first left-side opening 48l and a first right-side wire accommodating groove 49r continuous with a first right-side opening 48r at positions rotated 90 degrees around the insertion axis O with respect to those portions.

Figure 17:
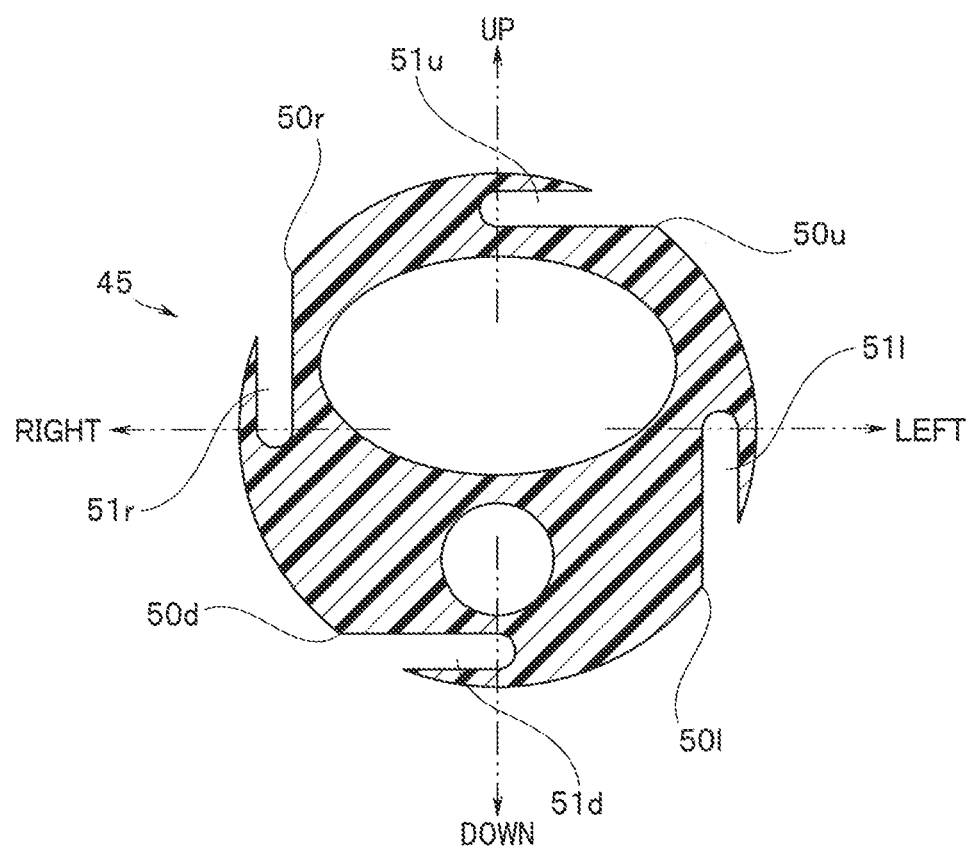
FIG. 17 relates to the fifth modification and is a cross-sectional view of main parts of the second bending piece of the bending portion shown by removing the sheath and the braid.

As illustrated, for example, in FIG. 17, the second bending piece 46 is provided with not only the second upper-side wire accommodating groove 51u continuous with the second upper-side opening 50u and the second lower-side wire accommodating groove 51d continuous with the second lower-side opening 50d, but also a second left-side wire accommodating groove 51l continuous with the second left-side opening 50l and a second right-side wire accommodating groove 51r continuous with the second right-side opening 50r at positions rotated 90 degrees around the insertion axis O with respect to those portions.

Note that the present invention is not limited to the embodiment described so far, but various modifications and changes can be made, and such modifications and changes are also included in the technical scope of the present invention. For example, a configuration of the bending tube in which a plurality of bending pieces are integrally formed by resin molding in the aforementioned embodiment, but the present invention is not limited to this, and it is also possible to constitute a bending tube, for example, by connecting a plurality of press-molded bending pieces using rivets or the like. It goes without saying that it is possible to combine the configuration of the aforementioned embodiment and the configuration of each modification as appropriate.

What is claimed is:
1. An endoscope bending portion comprising:
a plurality of bending elements connected in a longitudinal axis direction; and a first pulling wire configured to bend the plurality of bending elements in a first bending direction;
wherein a first bending element of the plurality of bending elements comprising:
a first outer circumferential surface;
a first inner circumferential surface; and
a first wire accommodating groove extending from a first opening on the first outer circumferential surface;
wherein the first wire accommodating groove is entirely disposed between the first outer circumferential surface and the first inner circumferential surface;
a second bending element of the plurality of bending elements comprising:
a second outer circumferential surface;
a second inner circumferential surface; and
a second wire accommodating groove extending from a second opening on the second outer circumferential surface;
wherein the second wire accommodating groove is entirely disposed between the second outer circumferential surface and the second inner circumferential surface;
wherein the first bending element and the second bending element are disposed adjacent to each other in the longitudinal axis direction,
the first pulling wire is disposed in both of the first and second wire accommodating grooves, and
the first opening of the first accommodating groove opens in a different direction from the second opening of the second accommodating groove.

2. The endoscope bending portion according to claim 1, wherein
the first wire accommodating groove extending from the first opening on the first outer circumferential surface in a first direction on a first side relative to a first bending plane having the first bending direction; and
the second wire accommodating groove extending from the second opening on the second outer circumferential surface in a second direction on a second side relative to the first bending plane, the second side being opposite to the first side.

3. The endoscope bending portion according to claim 2, wherein
the first direction is orthogonal relative to the first bending plane, and
the second direction is orthogonal relative to the first bending plane.

4. The endoscope bending portion according to claim 1, wherein the plurality of bending elements are integrally formed as a single unitary member.

5. The endoscope bending portion according to claim 1, wherein
the first wire accommodating groove having a first side surface and a second side surface opposing the first side surface; and
the second wire accommodating groove having a third side surface and a fourth side surface opposing the third side surface.

6. The endoscope bending portion according to claim 5, wherein
the first side surface and the second side surface are parallel to each other; and
the third side surface and the fourth side surface are parallel to each other.

7. The endoscope bending portion according to claim 1, further comprising a second pulling wire configured to bend the plurality of bending elements in a second bending direction opposite to the first bending direction;
wherein the first bending element of the plurality of bending elements further comprising:
a third wire accommodating groove extending from a third opening on the first outer circumferential surface;
wherein the third wire accommodating groove is entirely disposed between the first outer circumferential surface and the first inner circumferential surface;
the second bending element of the plurality of bending elements further comprising:
a fourth wire accommodating groove extending from a fourth opening on the second outer circumferential surface;
wherein the fourth wire accommodating groove is entirely disposed between the second outer circumferential surface and the second inner circumferential surface; and
the second pulling wire is disposed in both of the third and fourth wire accommodating grooves.

8. The endoscope bending portion according to claim 7, wherein
the third wire accommodating groove extending from the third opening on the first outer circumferential surface in the second direction on the second side relative to the first bending plane having the first bending direction and the second bending direction; and
the fourth wire accommodating groove extending from the fourth opening on the second outer circumferential surface in the first direction on the first side relative to the first bending plane.

9. The endoscope bending portion according to claim 7, wherein
the third wire accommodating groove having a first side surface and a second side surface opposing the first side surface; and
the fourth wire accommodating groove having a third side surface and a fourth side surface opposing the third side surface.

10. The endoscope bending portion according to claim 9, wherein
the first side surface and the second side surface are parallel to each other; and
the third side surface and the fourth side surface are parallel to each other.

11. The endoscope bending portion according to claim 7, wherein
the second pulling wire is disposed in both the third wire accommodating groove and the fourth wire accommodating groove; and
the third opening of the third groove opens in a different direction from the fourth opening of the fourth groove.

12. The bending portion according to claim 1, wherein
the first bending element includes a first hole and a second hole, at least one of which defining the first inner circumferential surface; and
the first hole and the second hole have a center aligned with the first bending plane.

13. The bending portion according to claim 1, wherein
the second bending element includes a first hole and a second hole, at least one of which defining the second inner circumferential surface; and the first hole and the second hole have a center aligned with the first bending plane.

14. An endoscope comprising:
an insertion portion comprising the bending portion according to claim 1.

15. An endoscope bending portion comprising a plurality of bending elements connected in a longitudinal axis direction; and
a first pulling wire configured to bend the plurality of bending elements in a first bending direction;
wherein a first bending element of the plurality of bending elements comprising:
a first outer circumferential surface;
a first inner circumferential surface; and
a first wire accommodating groove extending from a first opening on the first outer circumferential surface;
wherein the first wire accommodating groove extending from the first opening on the first outer circumferential surface in a first direction on a first side relative to a first bending plane having the first bending direction;
a second bending element of the plurality of bending elements comprising:
a second outer circumferential surface;
a second inner circumferential surface; and
a second wire accommodating groove extending from a second opening on the second outer circumferential surface;
wherein the second wire accommodating groove extending from the second opening on the second outer circumferential surface in a second direction on a second side relative to the first bending plane, the second side being opposite to the first side;
wherein the first bending element and the second bending element are disposed adjacent to each other in the longitudinal axis direction, and
the first pulling wire is disposed in both of the first and second wire accommodating grooves.

16. The bending portion according to claim 15, wherein the first wire accommodating groove is entirely disposed between the first outer circumferential surface and the first inner circumferential surface.

17. The bending portion according to claim 15, wherein the second wire accommodating groove is entirely disposed between the second outer circumferential surface and the second inner circumferential surface.

18. The endoscope bending portion according to claim 15, further comprising a second pulling wire configured to bend the plurality of bending elements in a second bending direction opposite to the first bending direction;
wherein the first bending element of the plurality of bending elements further comprising:
a third wire accommodating groove extending from a third opening on the first outer circumferential surface;
wherein the third wire accommodating groove extending from the third opening on the first outer circumferential surface in the second direction on the second side relative to the first bending plane having the first bending direction and the second bending direction;
the second bending element of the plurality of bending elements further comprising:
a fourth wire accommodating groove extending from a fourth opening on the second outer circumferential surface;
the fourth wire accommodating groove extending from the fourth opening on the second outer circumferential surface in the first direction on the first side relative to the first bending plane;
the second pulling wire is disposed in both of the third and fourth wire accommodating grooves.

19. The endoscope bending portion according to claim 18, wherein the third wire accommodating groove is entirely disposed between the first outer circumferential surface and the first inner circumferential surface;
wherein the fourth wire accommodating groove is entirely disposed between the second outer circumferential surface and the second inner circumferential surface.

* * * * *